(12) United States Patent
Potts et al.

(10) Patent No.: US 6,882,940 B2
(45) Date of Patent: Apr. 19, 2005

(54) METHODS AND DEVICES FOR PREDICTION OF HYPOGLYCEMIC EVENTS

(75) Inventors: Russell O. Potts, San Francisco, CA (US); Michael J. Tierney, San Jose, CA (US)

(73) Assignee: Cygnus, Inc., Redwood City, CA (US)

( * ) Notice: Subject to any disclaimer, the term of this patent is extended or adjusted under 35 U.S.C. 154(b) by 157 days.

(21) Appl. No.: 09/927,773

(22) Filed: Aug. 10, 2001

(65) Prior Publication Data

US 2002/0106709 A1 Aug. 8, 2002

Related U.S. Application Data

(60) Provisional application No. 60/226,431, filed on Aug. 18, 2000.

(51) Int. Cl.$^7$ ............... G01N 33/487; G06F 17/00; A61B 5/00; C12Q 1/54
(52) U.S. Cl. ............... 702/23; 712/32; 435/14; 600/347
(58) Field of Search ............... 702/22, 19, 23; 712/32; 435/14; 600/347

(56) References Cited

U.S. PATENT DOCUMENTS

| | | | |
|---|---|---|---|
| 4,509,531 A | 4/1985 | Ward | |
| 5,279,543 A | 1/1994 | Glikfeld et al. | 604/20 |
| 5,362,307 A | 11/1994 | Guy et al. | 604/20 |
| 5,735,273 A | 4/1998 | Kurnik et al. | 128/635 |
| 5,747,806 A | 5/1998 | Khalil et al. | 250/339.12 |
| 5,760,714 A | 6/1998 | Zimmerman | 341/26 |
| 5,771,890 A | 6/1998 | Tamada | 128/635 |
| 5,792,668 A | 8/1998 | Fuller et al. | |
| 5,827,183 A | 10/1998 | Kurnik et al. | 600/345 |
| 5,954,685 A | 9/1999 | Tierney | 604/20 |
| 5,989,408 A | 11/1999 | Baerts et al. | 205/783.5 |
| 6,023,629 A | 2/2000 | Tamada | 600/347 |
| 6,139,718 A | 10/2000 | Kurnik et al. | 205/777.5 |
| 6,141,573 A | 10/2000 | Kurnik et al. | 600/345 |
| 6,144,869 A | 11/2000 | Berner et al. | 600/347 |
| 6,180,416 B1 | 1/2001 | Kurnik et al. | 435/14 |
| 6,201,979 B1 | 3/2001 | Kurnik et al. | 600/345 |
| 6,233,471 B1 | 5/2001 | Berner et al. | 600/345 |
| 6,272,364 B1 | 8/2001 | Kurnik | 600/345 |
| 6,284,126 B1 | 9/2001 | Kurnik et al. | 205/777.5 |
| 6,298,254 B1 | 10/2001 | Tamada | 600/347 |
| 6,299,578 B1 | 10/2001 | Kurnik et al. | 600/309 |
| 6,309,351 B1 | 10/2001 | Kurnik et al. | 600/309 |
| 6,326,160 B1 | 12/2001 | Dunn et al. | 435/14 |

FOREIGN PATENT DOCUMENTS

| | | |
|---|---|---|
| DE | 42 21 848 A1 | 1/1994 |
| WO | WO 96/00109 | 1/1996 |
| WO | WO 97/02811 | 1/1997 |
| WO | WO 97/39341 | 10/1997 |
| WO | WO 99/58190 | 11/1999 |
| WO | WO 99/58973 | 11/1999 |

OTHER PUBLICATIONS

Bolinger, Robert E., "Galvanic Skin Reflex and Plasma Free Fatty Acids During Insulin Reactions," *Diabetes* 13(6):600–605 (1964).
Davies et al, "Sweat Detection as an Indicator of Nocturnal Hypoglycaemia," *Lancet* 346:772 (1995).
Levandoski et al, "Teledyne Sleep Sentry ®—A Possible Aid for the Detection of Symptomatic Nocturnal Hypoglycemia in Insulin–Dependent Diabetics," *Artificial Systems for Insulin Delivery*, 353–356 (1983).
Pickup, J.C., "Preliminary Evaluation of a Skin Conductance Meter for Detecting Hypoglycemia in Diabetic Patients," *Diabetic Care* 5: 326–329, (1982).
Tierney et al, "The GlucoWatch ® Biographer: A Frequent, Automatic and Non–invasive Glucose Monitor," *Ann Med* 2000; 32: 632–641.
Tierney et al, "Effect of Acetaminophen on the Accuracy of Glucose Measurements Obtained with the GlucoWatch Biographer," *Diabetes Technology & Therapeutics* 2(2):199–207 (2000).
Bolinder et al., *Diabetes Care* 20:64–70 (1997).
Newman et al., "Catalytic Materials, Membranes, and Fabrication Technologies Suitable for the Construction of Amperometric Biosensors," *Analytical Chemistry* 67:4594–4599 (1995).
Ohkubo et al., *Diabetes Research & Clinical Practice* 28:103–117 (1995).
Tamada et al., "Noninvasive Glucose Monitoring," *JAMA* 282:1839–1844 (1999).
UK Prospective Diabetes Study (UKPDS) Group. *Lancet* 352:837–853 (1998).
Updike et al., "The Enzyme Electrode," *Nature* 214:986–988 (1967).

*Primary Examiner*—Marjorie Moran
(74) *Attorney, Agent, or Firm*—Barbara G. McClung; Gary R. Fabian

(57) ABSTRACT

Described herein are methods, devices, and microprocessors useful for predicting a hypoglycemic event in a subject. The hypoglycemic predictive approach described herein utilizes information obtained from a data stream, e.g., frequently obtained glucose values (current and/or predicted), body temperature, and/or skin conductance, to predict incipient hypoglycemic events and to alert the user.

34 Claims, 3 Drawing Sheets

METHODS AND DEVICES FOR PREDICTION OF HYPOGLYCEMIC EVENTS

CROSS-REFERENCE TO RELATED APPLICATIONS

This application is related to U.S. Provisional Patent Application Ser. No. 60/226,431, filed Aug. 18, 2000, from which priority is claimed under 35 USC § 119(e)(1), and which application is incorporated herein by reference in its entirety.

TECHNICAL FIELD

Described herein are methods, devices, and microprocessors useful for predicting a hypoglycemic event in a subject. The present invention for prediction of hypoglycemic events typically employs multiple parameters in the prediction. Such parameters include, but are not limited to, glucose readings (current and/or predicted), body temperature, and/or skin conductance.

BACKGROUND OF THE INVENTION

Hypoglycemia is the most critical acute complication of diabetes. Typically used present methods of self-monitoring of blood glucose (SMBG) provide periodic measurements of blood glucose obtained from a finger stick. This method produces measurements that, while very accurate, are too infrequent to detect hypoglycemic episodes. Frequently, in order to avoid hypoglycemia, diabetics maintain abnormally high blood glucose levels to provide a "buffer" against low blood glucose levels. This constant high blood glucose level is the root cause of most long-term complications of diabetes, namely, retinopathy, neuropathy, nephropathy, and cardiovascular disease. In effect, the present SMBG methods are forcing many diabetics to pay for a lower rate of acute complications with a higher rate of chronic complications in later life.

The Diabetes Control and Complications Trial (DCCT) (The Diabetes Control and Complications Trial Research Group. New Engl. J. Med. 329, 977–1036 (1993)) clearly showed that more blood glucose information is essential to better clinical outcomes. The subject group that measured blood glucose and administered insulin more frequently (3–7 times per day) had a substantially lower rate of complications at the end of the study relative to the group that tested and injected less frequently. Even so, the tight control group was only able to reduce the average blood glucose to a value approximately 50% above normal (153 mg/dL). Similarly, the HbA1c levels (a measure of average blood glucose level over time) were lowered substantially relative to the control group, but not into the normal range. As a result of this more intensive therapy, the tight control group experienced hypoglycemic events three times more often than the control group. These results demonstrate that three to seven blood glucose measurements per day are sufficient to lower longer-term complication rates, but still do not provide enough information to bring average blood glucose levels to normal, or to prevent hypoglycemic events. Similar results have been obtained for subjects on oral medication (UK Prospective Diabetes Study (UKPDS) Group, Lancet 352:837–853 (1998); Ohkubo Y, et al., Diabetes Research & Clinical Practice 28:103–17 (1995)), demonstrating the general benefit of frequent glucose monitoring in the management of diabetes. However, Bolinder, et al., (Diabetes Care 20:64–70 (1997)) show that even seven measurements per day fail to detect more than one-third of all hypoglycemic events.

SUMMARY OF THE INVENTION

The present invention describes methods, devices, and microprocessors for predicting a hypoglycemic event in a subject. The methods of the invention typically employ multiple parameters to be used in prediction of the hypoglycemic event. Such parameters include, but are not limited to, current glucose readings (reflecting glucose amount or concentration in the subject), one or more predicted future glucose reading, body temperature, and skin conductance.

In one aspect the present invention comprises a method for predicting a hypoglycemic event in a subject. The method comprises determining threshold values (or ranges of values) for the selected parameters, wherein the threshold values (or ranges of values) are indicative of a hypoglycemic event in the subject: e.g., determining (i) a threshold glucose value (or range of values) that corresponds to the hypoglycemic event, and (ii) at least one threshold parameter value that is correlated with the hypoglycemic event, wherein the parameter is either skin conductance readings or temperature readings. In one embodiment of the invention both skin conductance readings and temperature readings are employed. A series of glucose measurement values is typically obtained at selected time intervals. In one embodiment the time intervals are evenly spaced. Such a series may be obtained, for example, using a method comprising: extracting a sample comprising glucose from the subject using a transdermal sampling system that is in operative contact with a skin or mucosal surface of the subject; obtaining a raw signal from the extracted glucose, wherein the raw signal is specifically related to glucose amount or concentration in the subject; correlating the raw signal with a glucose measurement value indicative of the amount or concentration of glucose present in the subject at the time of extraction; and repeating the extracting, obtaining, and correlating to provide a series of measurement values at selected time intervals. In one embodiment, the sampling system is maintained in operative contact with the skin or mucosal surface of the subject during the extracting, obtaining, and correlating to provide for frequent glucose measurements.

In the practice of this aspect of the method, either the current glucose value (time=n) or a measurement value predicted for a further time interval subsequent to the series of measurement values (e.g., time=n+1; that is, one time interval after the most recent measurement (time=n) in the series of measurement values), is compared to the threshold glucose value, wherein a measurement value lower than or equal to the threshold value is designated to be hypoglycemic.

A parameter value or trend of parameter values is measured concurrently, simultaneously, or sequentially with the obtaining of the series of glucose measurement values. In one embodiment of the invention, the parameter value or trend of parameter values is reflective of either skin conductance readings or temperature readings of the subject. The parameter value or trend of parameter values is compared with the threshold parameter value (or range of values) to determine whether the parameter value or trend of parameter values indicates a hypoglycemic event. A hypoglycemic event is predicted in the subject when both (i) comparing the predicted measurement value to the threshold glucose value indicates a hypoglycemic event, and (ii) comparing one or more other parameter (e.g., body temperature and/or skin conductance) with the threshold parameter value (or range of values) indicates a hypoglycemic event.

In one embodiment of the above method, the series of measurement values comprises three or more discrete values. In this embodiment, the predicting of the measurement value at a further time interval may be carried out using the series of three or more measurement values in a series function represented by:

$$y_{n+1} = y_n + \alpha(y_n - y_{n-1}) + \frac{\alpha^2}{2}(y_n - 2y_{n-1} + y_{n-2}) \qquad (7)$$

wherein y is the measurement value of glucose, n is the time interval between measurement values, and α is a real number between 0 and 1. The series function may be used to predict the value of $y_{n+1}$ where the time interval n+1 occurs one time interval after the series of measurement values is obtained.

When skin conductance is a selected parameter, the sampling system typically comprises a sweat probe and the skin conductance readings are obtained using the sweat probe.

When body temperature is a selected parameter, the sampling system typically comprises a temperature probe and the temperature readings are obtained using the temperature probe.

In one embodiment of the method of the present invention, the sample comprising glucose is extracted from the subject into a collection reservoir to obtain an amount or concentration of glucose in the reservoir. Such one or more collection reservoirs are typically in contact with the skin or mucosal surface of the subject and the sample is extracted using an iontophoretic current applied to the skin or mucosal surface. Further, at least one collection reservoir may comprise an enzyme that reacts with the extracted glucose to produce an electrochemically detectable signal, e.g., glucose oxidase. Alternatively, the series of glucose measurement values may be obtained with a different device, for example, using a near-IR spectrometer.

The present invention also includes a glucose monitoring system useful for performing the methods of the present invention. In one embodiment, the glucose monitoring system comprises, in operative combination, a sensing mechanism (in operative contact with the subject or with a glucose-containing sample extracted from the subject, wherein the sensing mechanism obtains a raw signal specifically related to glucose amount or concentration in the subject), a device to obtain either skin conductance readings or temperature readings from the subject, and one or more microprocessors in operative communication with the sensing mechanism. The microprocessors comprise programming to (i) control the sensing mechanism to obtain a series of raw signals at selected time intervals, (ii) correlate the raw signals with measurement values indicative of the amount or concentration of glucose present in the subject to obtain a series of measurement values, (iii) when necessary predict a measurement value at a further time interval, which occurs after the series of measurement values is obtained, (iv) compare the predicted measurement value to a predetermined threshold value or range of values, wherein a predicted measurement value lower than the predetermined threshold value is designated to be hypoglycemic, (v) control the device for measuring skin conductance readings or temperature readings of the subject, (vi) compare the skin conductance readings or temperature readings with a threshold parameter value, range of values, or trend of parameter values to determine whether the skin conductance readings or temperature readings indicate a hypoglycemic event; and (vii) predict a hypoglycemic event in the subject when both (a) comparing the predicted measurement value to the threshold glucose value (or range of values) indicates a hypoglycemic event, and (b) comparing the skin conductance readings and/or temperature readings with a threshold parameter value, range of values, or trend of parameter values indicates a hypoglycemic event.

The sensing mechanism of the monitoring system may, for example, comprise a biosensor having an electrochemical sensing element or a near-IR spectrometer. Further, the monitoring system may comprise a device to obtain the skin conductance readings (e.g., a sweat probe) and/or a device to obtain the temperature readings (e.g., a temperature probe).

In one embodiment of the monitoring system, the predicting of a measurement value at a further time interval is carried out using the series of three or more measurement values in a series function represented by:

$$y_{n+1} = y_n + \alpha(y_n - y_{n-1}) + \frac{\alpha^2}{2}(y_n - 2y_{n-1} + y_{n-2}) \qquad (7)$$

wherein y is the measurement value of glucose, n is the time interval between measurement values, and α is a real number between 0 and 1.

In one aspect of the present invention, the method for prediction of hypoglycemic events employs a decision tree that utilizes a hierarchical evaluation of thresholds of selected parameters, where the thresholds are indicative of a hypoglycemic event. Such parameters include, but are not limited to, current glucose readings (reflecting glucose amount or concentration in the subject), one or more predicted future glucose reading, body temperature, and skin conductance. In another aspect, the present invention comprises one or more microprocessors programmed to control the above described methods, measurement cycle, devices, mechanisms, calculations, predictions, comparisons, evaluations, etc. The microprocessors may also mediate an alarm or alert related to the predicted hypoglycemic event.

These and other embodiments of the present invention will readily occur to those of ordinary skill in the art in view of the disclosure herein.

DETAILED DESCRIPTION OF THE INVENTION

Figure 1:
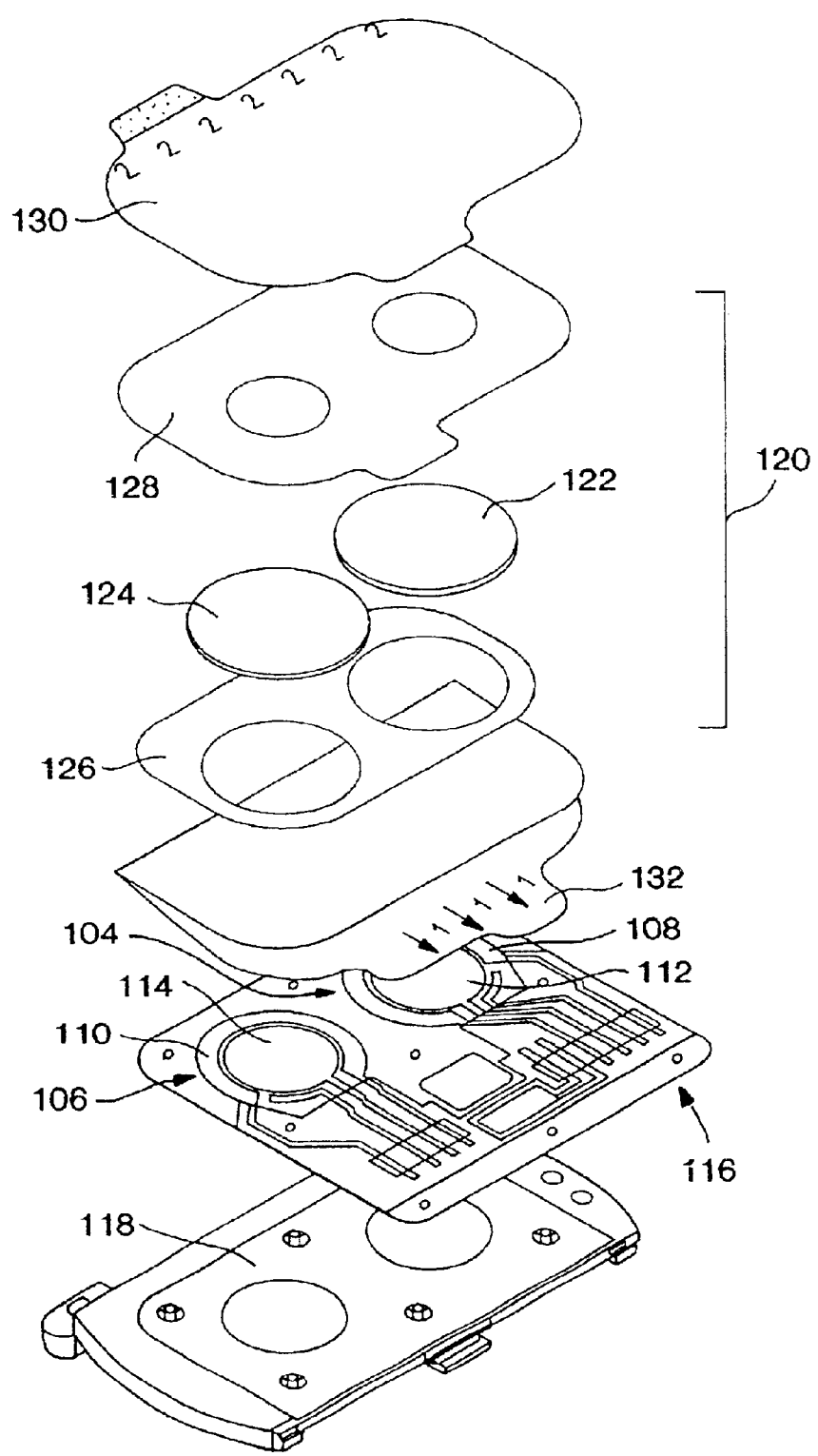
FIG. 1 presents a schematic diagram of a skin-side view of the GlucoWatch® (Cygnus, Inc., Redwood City, Calif., US) biographer system.

The practice of the present invention will employ, unless otherwise indicated, conventional methods of diagnostics, chemistry, biochemistry, electrochemistry, statistics, and pharmacology, within the skill of the art in view of the teachings of the present specification. Such conventional methods are explained fully in the literature.

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "a reservoir" includes a combination of two or more such reservoirs, reference to "an analyte" includes mixtures of analytes, and the like.

1. Definitions

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "microprocessor" refers to a computer processor contained on an integrated circuit chip, such a processor may also include memory and associated circuits. A microprocessor may further comprise programmed instructions to execute or control selected functions, computational methods, switching, etc. Microprocessors and associated devices are commercially available from a number of sources, including, but not limited to, Cypress Semiconductor Corporation, San Jose, Calif.; IBM Corporation, White Plains, N.Y.; Applied Microsystems Corporation, Redmond, Wash.; Intel Corporation, Chandler, Ariz.; NEC Corporation, New York, N.Y.; and, National Semiconductor, Santa Clara, Calif.

The terms "analyte" and "target analyte" are used to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device," "sampling mechanism" or "sampling system" refers to any device and/or associated method for obtaining a sample from a biological system for the purpose of determining the concentration of an analyte of interest. Such "biological systems" include any biological system from which the analyte of interest can be extracted, including, but not limited to, blood, interstitial fluid, perspiration and tears. Further, a "biological system" includes both living and artificially maintained systems. The term "sampling" mechanism refers to extraction of a substance from the biological system, generally across a membrane such as the stratum corneum or mucosal membranes, wherein said sampling is invasive, minimally invasive, semi-invasive or non-invasive. The membrane can be natural or artificial, and can be of plant or animal nature, such as natural or artificial skin, blood vessel tissue, intestinal tissue, and the like. Typically, the sampling mechanism is in operative contact with a "reservoir," or "collection reservoir," wherein the sampling mechanism is used for extracting the analyte from the biological system into the reservoir to obtain the analyte in the reservoir. Non-limiting examples of sampling techniques include iontophoresis, sonophoresis (see, e.g., International Publication No. WO 91/12772, published 5 Sep. 1991; U.S. Pat. No. 5,636,632), suction, electroporation, thermal poration, passive diffusion (see, e.g., International Publication Nos.: WO 97/38126 (published 16 Oct. 1997); WO 97/42888, WO 97/42886, WO 97/42885, and WO 97/42882 (all published 20 Nov. 1997); and WO 97/43962 (published 27 Nov. 1997)), microfine (miniature) lances or cannulas, biolistic (e.g., using particles accelerated to high speeds), subcutaneous implants or insertions, and laser devices (see, e.g., Jacques et al. (1978) J. Invest. Dermatology 88:88–93; International Publication WO 99/44507, published 10 Sep. 1999; International Publication WO 99/44638, published 10 Sep. 1999; and International Publication WO 99/40848, published Aug. 19, 1999 ). Iontophoretic sampling devices are described, for example, in International Publication No. WO 97/24059, published 10 Jul. 1997; European Patent Application EP 0942 278, published 15 Sep. 1999; International Publication No. WO 96/00110, published 4 Jan. 1996; International Publication No. WO 97/10499, published 3 Mar. 1997; U.S. Pat. Nos. 5,279,543; 5,362,307; 5,730,714; 5,771,890; 5,989,409; 5,735,273; 5,827,183; 5,954,685 and 6,023,629, all of which are herein incorporated by reference in their entireties. Further, a polymeric membrane may be used at, for example, the electrode surface to block or inhibit access of interfering species to the reactive surface of the electrode.

The term "physiological fluid" refers to any desired fluid to be sampled, and includes, but is not limited to, blood, cerebrospinal fluid, interstitial fluid, semen, sweat, saliva, urine and the like.

The term "artificial membrane" or "artificial surface," refers to, for example, a polymeric membrane, or an aggregation of cells of monolayer thickness or greater which are grown or cultured in vivo or in vitro, wherein said membrane or surface functions as a tissue of an organism but is not actually derived, or excised, from a pre-existing source or host.

A "monitoring system" or "analyte monitoring device" refer to a system useful for obtaining frequent measurements of a physiological analyte present in a biological system. Such a device is useful, for example, for monitoring the amount or concentration of an analyte in a subject. Such a system may comprise, but is not limited to, a sampling mechanism, a sensing mechanism, and a microprocessor mechanism in operative communication with the sampling mechanism and the sensing mechanism. Such a device typically provides frequent measurement or determination of analyte amount or concentration in the subject and provides an alert or alerts when levels of the analyte being monitored fall outside of a predetermined range. Such devices may comprise durable and consumable (or disposable) elements. The term "glucose monitoring device" refers to a device for monitoring the amount or concentration of glucose in a subject. Such a device typically provides a frequent measurement or determination of glucose amount or concentration in the subject and provides an alert or alerts when glucose levels fall outside of a predetermined range. One such exemplary glucose monitoring device is the GlucoWatch biographer available from Cygnus, Inc., Redwood City, Calif., US. The GlucoWatch biographer comprises two primary elements, a durable element (comprising a watch-type housing, circuitry, display element, microprocessor element, electrical connector elements, and may further comprise a power supply) and a consumable, or disposable, element (e.g., an AutoSensor component involved in sampling and signal detection, see, for example, WO 99/58190, published 18 Nov. 1999). This and similar devices is described, for example, in the following publications: Tamada, et al., (1999) *JAMA* 282:1839–1844; U.S. Pat. No. 5,771,890, issued 30 Jun. 1998; U.S. Pat. No. 5, 735,273, issued 7 Apr. 1998; U.S. Pat. No. 5,827,183, issued 27 Oct. 1998; U.S. Pat. No. 5,954,685, issued 21 Sep. 1999; U.S. Pat. No. 5,989,409, issued 23 Nov. 1999; U.S. Pat. No. 6,023,629, issued 8 Feb. 2000; EP Patent Application EP 0 942 278 A2, published 15 Sept. 1999; PCT International Application WO 96/001 100, published 1 Jan. 1996; PCT International Application WO 99/58190, published 18 Nov. 1999. The GlucoWatch biographer provides a device for frequent sampling of glucose from a subject the application of low intensity electric fields across the skin (iontophoresis) to enhance the transport of glucose from body tissues to a sampling chamber. In addition, when the concentration or amount of glucose has been determined to be outside of a predetermined range of values the GlucoWatch biographer produces an alert or alarm signal. Such an alert or alarm is a component of the GlucoWatch biographer.

A "measurement cycle" typically comprises extraction of an analyte from a subject, using, for example, a sampling device, and sensing of the extracted analyte, for example, using a sensing device, to provide a measured signal, for example, a measured signal response curve. A complete measurement cycle may comprise one or more sets of extraction and sensing.

The term "frequent measurement" refers to a series of two or more measurements obtained from a particular biological system, which measurements are obtained using a single device maintained in operative contact with the biological system over a time period in which a series of measurements (e.g, second, minute or hour intervals) is obtained. The term thus includes continual and continuous measurements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

The term "transdermal" includes both transdermal and transmucosal techniques, i.e., extraction of a target analyte across skin, e.g., stratum corneum, or mucosal tissue. Aspects of the invention which are described herein in the context of "transdermal," unless otherwise specified, are meant to apply to both transdermal and transmucosal techniques.

The term "transdermal extraction," or "transdermally extracted" refers to any sampling method, which entails extracting and/or transporting an analyte from beneath a tissue surface across skin or mucosal tissue. The term thus includes extraction of an analyte using, for example, iontophoresis (reverse iontophoresis), electroosmosis, sonophoresis, microdialysis, suction, and passive diffusion. These methods can, of course, be coupled with application of skin penetration enhancers or skin permeability enhancing technique such as various substances or physical methods such as tape stripping or pricking with micro-needles. The term "transdermally extracted" also encompasses extraction techniques which employ thermal poration, laser microporation, electroporation, microfine lances, microfine cannulas, subcutaneous implants or insertions, combinations thereof, and the like.

The term "iontophoresis" refers to a method for transporting substances across tissue by way of an application of electrical energy to the tissue. In conventional iontophoresis, a reservoir is provided at the tissue surface to serve as a container of (or to provide containment for) material to be transported. Iontophoresis can be carried out using standard methods known to those of skill in the art, for example by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode). For example, see U.S. Pat. Nos. 5,771,890 and 6,023,629 and PCT Publication No. WO 96/00109, published 4 Jan. 1996.

The term "reverse iontophoresis" refers to the movement of a substance from a biological fluid across a membrane by way of an applied electric potential or current. In reverse iontophoresis, a reservoir is provided at the tissue surface to receive the extracted material, as used in the GlucoWatch biographer glucose monitor (See, e.g., Tamada et al. (1999) JAMA 282:1839–1844; Cygnus, Inc., Redwood City, Calif.).

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," or "sensing mechanism," encompasses any device that can be used to measure the concentration or amount of an analyte, or derivative thereof, of interest. The sensing mechanism may employ any suitable sensing element to provide the raw signal (where the raw signal is specifically related to analyte amount or concentration) including, but not limited to, physical, chemical, electrochemical, photochemical, spectrophotometric, polarimetric, colorimetric, radiometric, or like elements, and combinations thereof. Examples of electrochemical devices include the Clark electrode system (see, e.g., Updike, et al., (1967) Nature 214:986–988), and other amperometric, coulometric, or potentiometric electrochemical devices, as well as, optical methods, for example UV detection or infrared detection (e.g., U.S. Pat. No. 5,747,806). Further examples include, a near-IR radiation diffuse-reflection laser spectroscopy device (e.g, described in U.S. Pat. No. 5,267,152 to Yang, et al.). Similar near-IR spectrometric devices are also described in U.S. Pat. No. 5,086,229 to Rosenthal, et al. and U.S. Pat. No. 4,975,581 to Robinson, et al. These near-IR devices use traditional methods of reflective or transmissive near infrared (near-IR) analysis to measure absorbance at one or more glucose-specific wavelengths, and can be contacted with the subject at an appropriate location, such as a finger-tip, skin fold, eyelid, or forearm surface to obtain the raw signal. In preferred embodiments of the invention, a biosensor is used which comprises an electrochemical sensing element.

A "biosensor" or "biosensor device" includes, but is not limited to, a "sensor element" that includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, and silver, as well as, oxides, and dioxides, thereof, and combinations or alloys of the foregoing, which may include carbon as well. Some catalytic materials, membranes, and fabrication technologies suitable for the construction of amperometric biosensors are described by Newman, J. D., et al.(1995) Analytical Chemistry 67:4594–4599.

The "sensor element" can include components in addition to the sensing electrode, for example, it can include a "reference electrode" and a "counter electrode." The term "reference electrode" is used to mean an electrode that provides a reference potential, e.g., a potential can be established between a reference electrode and a working electrode. The term "counter electrode" is used to mean an electrode in an electrochemical circuit that acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are preferred.

In one embodiment, the "counter electrode" of the "sensor element" comprises a "bimodal electrode." The term "bimodal electrode" typically refers to an electrode which is capable of functioning non-simultaneously as, for example, both the counter electrode (of the "sensor element") and the iontophoretic electrode (of the "sampling mechanism") as described, for example, U.S. Pat. No. 5,954,685.

The terms "reactive surface," and "reactive face" are used interchangeably herein to mean the surface of the sensing electrode that: (1) is in contact with the surface of an ionically conductive material which contains an analyte or through which an analyte, or a derivative thereof, flows from a source thereof; (2) is comprised of a catalytic material (e.g., a platinum group metal, platinum, palladium, rhodium, ruthenium, or nickel and/or oxides, dioxides and combinations or alloys thereof) or a material that provides sites for electrochemical reaction; (3) converts a chemical signal (for example, hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

An "ionically conductive material" refers to any material that provides ionic conductivity, and through which electrochemically active species can diffuse. The ionically conductive material can be, for example, a solid, liquid, or semisolid (e.g., in the form of a gel) material that contains an electrolyte, which can be composed primarily of water and ions (e.g., sodium chloride), and generally comprises 50% or more water by weight. The material can be in the form of a hydrogel, a sponge or pad (e.g., soaked with an electrolytic solution), or any other material that can contain an electrolyte and allow passage of electrochemically active species, especially the analyte of interest. Some exemplary hydrogel formulations are described in WO 97/02811, published Jan. 30, 1997. The ionically conductive material may comprise a biocide. For example, during manufacture of an AutoSensor assembly, one or more biocides may be incorporated into the ionically conductive material. Biocides of interest include, but are not limited to, compounds such as chlorinated hydrocarbons; organometallics; hydrogen releasing compounds; metallic salts; organic sulfur compounds; phenolic compounds (including, but not limited to, a variety of Nipa Hardwicke Inc. liquid preservatives registered under the trade names Nipastat®, Nipaguard®, Phenosept®, Phenonip®, Phenoxetol®, and Nipacide®); quaternary ammonium compounds; surfactants and other membrane-disrupting agents (including, but not limited to, undecylenic acid and its salts), combinations thereof, and the like.

The term "buffer" refers to one or more components which are added to a composition in order to adjust or maintain the pH of the composition.

The term "electrolyte" refers to a component of the ionically conductive medium which allows an ionic current to flow within the medium. This component of the ionically conductive medium can be one or more salts or buffer components, but is not limited to these materials.

The term "collection reservoir" is used to describe any suitable containment method or device for containing a sample extracted from a biological system. For example, the collection reservoir can be a receptacle containing a material which is ionically conductive (e.g., water with ions therein), or alternatively it can be a material, such as a sponge-like material or hydrophilic polymer, used to keep the water in place. Such collection reservoirs can be in the form of a hydrogel (for example, in the shape of a disk or pad). Hydrogels are typically referred to as "collection inserts." Other suitable collection reservoirs include, but are not limited to, tubes, vials, strips, capillary collection devices, cannulas, and miniaturized etched, ablated or molded flow paths.

A "collection insert layer" is a layer of an assembly or laminate comprising a collection reservoir (or collection insert) located, for example, between a mask layer and a retaining layer.

A "laminate" refers to structures comprised of, at least, two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, chemical compounds such as, cyanoacrylate adhesives, and epoxies, as well as adhesives having such physical attributes as, but not limited to, the following: pressure sensitive adhesives, thermoset adhesives, contact adhesives, and heat sensitive adhesives.

A "collection assembly" refers to structures comprised of several layers, where the assembly includes at least one collection insert layer, for example a hydrogel. An example of a collection assembly as referred to in the present invention is a mask layer, collection insert layer, and a retaining layer where the layers are held in appropriate functional relationship to each other but are not necessarily a laminate (i.e., the layers may not be bonded together. The layers may, for example, be held together by interlocking geometry or friction).

The term "mask layer" refers to a component of a collection assembly that is substantially planar and typically contacts both the biological system and the collection insert layer. See, for example, U.S. Pat. Nos. 5,735,273, 5,827,183, and 6,201,979, all herein incorporated by reference.

The term "gel retaining layer" or "gel retainer" refers to a component of a collection assembly that is substantially planar and typically contacts both the collection insert layer and the electrode assembly.

The term "support tray" typically refers to a rigid, substantially planar platform and is used to support and/or align the electrode assembly and the collection assembly. The support tray provides one way of placing the electrode assembly and the collection assembly into the sampling system.

An "AutoSensor assembly" refers to a structure generally comprising a mask layer, collection insert layer, a gel retaining layer, an electrode assembly, and a support tray. The AutoSensor assembly may also include liners where the layers are held in approximate, functional relationship to each other. Exemplary collection assemblies and AutoSensor structures are described, for example, in International Publication WO 99/58190, published 18 Nov. 1999; and U.S. Pat. Nos. 5,735,273 and 5,827,183. The mask and retaining layers are preferably composed of materials that are substantially impermeable to the analyte (chemical signal) to be detected; however, the material can be permeable to other substances. By "substantially impermeable" is meant that the material reduces or eliminates chemical signal transport (e.g., by diffusion). The material can allow for a low level of chemical signal transport, with the proviso that chemical signal passing through the material does not cause significant edge effects at the sensing electrode.

The terms "about" or "approximately" when associated with a numeric value refers to that numeric value plus or minus 10 units of measure (i.e. percent, grams, degrees or volts), preferably plus or minus 5 units of measure, more preferably plus or minus 2 units of measure, most preferably plus or minus 1 unit of measure.

By the term "printed" is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, electroplating, laminating, or the like.

The term "physiological effect" encompasses effects produced in the subject that achieve the purpose of a therapy. In preferred embodiments, a physiological effect means that the symptoms of the subject being treated are prevented or alleviated. For example, a physiological effect would be one that results in the prolongation of survival in a patient.

"Parameter" refers to an arbitrary constant or variable so appearing in a mathematical expression that changing it gives various cases of the phenomenon represented (McGraw-Hill Dictionary of Scientific and Technical Terms, S. P. Parker, ed., Fifth Edition, McGraw-Hill Inc., 1994). A parameter is any of a set of properties whose values determine the characteristics or behavior of something.

"Decay" refers to a gradual reduction in the magnitude of a quantity, for example, a current detected using a sensor electrode where the current is correlated to the concentration of a particular analyte and where the detected current gradually reduces but the concentration of the analyte does not.

"Skip" or "skipped" signals refer to data that do not conform to predetermined criteria (for example, error-associated criteria as described in U.S. Pat. No. 6,233,471, herein incorporated by reference). A skipped reading, signal, or measurement value typically has been rejected (i.e., a "skip error" generated) as not being reliable or valid because it does not conform with data integrity checks, for example, where a signal is subjected to a data screen which invalidates incorrect signals based on a detected parameter indicative of a poor or incorrect signal.

The term "Taylor Series Exponential Smoothing Function ("TSES")" encompasses mathematical functions (algorithms) for predicting the behavior of a variable at a different point in time, which factors in the slope, and the rate of change of the slope. An example of a TSES function useful in connection with the present invention is a TSES function represented by:

$$y_{n+1} = y_n + \alpha(y_n - y_{n-1}) + \frac{\alpha^2}{2}(y_n - 2y_{n-1} + y_{n-2})$$

wherein: $\alpha$ is an optimizable variable which is a real number of between 0 and 1, and is adjusted based on the particular measurements obtained and the relationship between those measurements and actual results; n is an evenly spaced time interval; and y is an analyte concentration or signal converted to an analyte concentration which signal measurement is optimized to fit the results sought, e.g., to correspond with a reference analyte concentration (see, for example, U.S. Pat. No. 6,272,364, issued 7 Aug. 2001; WO 99 58973, published 18 Nov. 1999; both herein incorporated by reference in their entireties).

A "future time point" refers to the time point in the future at which the concentration of the analyte of interest or another parameter value is predicted. In preferred embodiments, this term refers to a time point that is one time interval ahead, where a time interval is the amount of time between sampling and sensing events.

2.0 Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1 General Overview of the Invention

Hypoglycemia is the most important acute complication of diabetes and is a major obstacle to achieving optimal blood glucose control. Nocturnal hypoglycemia can be particularly troublesome for many patients. The research proposed here utilizes information obtained from a data stream, e.g., frequently obtained glucose values, skin conductance or temperature readings, generated by a frequent sampling glucose monitoring device, e.g., the GlucoWatch biographer system, coupled with a time-series forecasting approach, to predict incipient hypoglycemic events and to alert the user.

The invention is described herein with reference to the GlucoWatch biographer system as an exemplary glucose monitoring system capable of providing frequent readings of glucose amount or concentration for a user. The GlucoWatch biographer system extracts glucose through the skin via reverse iontophoresis and measures the extracted glucose with an amperometric biosensor. Glucose readings can be obtained, for example, every twenty minutes for a twelve-hour measurement period. Large-scale clinical trials of this device in diabetic subjects have been completed (Tierney, M. J., et al., Annals of Medicine, 32, 632–641 (2000); Tierney, M. J., et al., Diabetes Technology and Therapeutics, 2 (2), 197–205 (2000); Tamada, J. A., et al., J. Am. Med. Assoc. 282, 1839–44 (1999)).

A major disadvantage of the current paradigm of discrete blood glucose measurements for self-monitoring of blood glucose (SMBG) levels for diabetics is that the low number of measurements performed per day (on average 1.8 readings per day) is insufficient to track blood glucose excursions occurring between the measurements. More frequent monitoring is desirable both for determining the normal diurnal blood glucose profile, and for detection of hypoglycemic events. The GlucoWatch biographer system measures glucose levels every 20 minutes, and has been shown to track blood glucose levels accurately. In addition, the GlucoWatch biographer system sounds an audible alarm if the measured glucose level falls below a user-settable low glucose threshold, or if the measured glucose level falls rapidly between successive readings. Although the present Gluco-Watch biographer system is able to accurately detect the presence of hypoglycemic conditions, it is not currently able to predict hypoglycemic events in advance.

Experiments performed in support of the present invention indicate methods to improve the hypoglycemic event prediction ability of the GlucoWatch biographer system by combining (i) the continual stream of glucose readings, with other physiological measures that are indicators of hypoglycemia, for example, (ii) skin temperature and/or (iii) perspiration. In a preferred embodiment, combinations of these three physiological parameters results in a more robust predictor of hypoglycemia.

In addition, the method of the present invention employs a time-series forecasting algorithm. This technique uses several previous readings to predict with sufficient accuracy the glucose level a short time in the future. Therefore, this technique could be used to predict incipient hypoglycemia. The time-series forecasting algorithm has been described in co-owned, co-pending, WO 99/58973, published 18 Nov. 1999, herein incorporated by reference in its entirety. Predictions based on this method are combined with predictions based on the methods described above.

Accordingly, one aspect of the present invention may be summarized as follows. A series of conditional statements leading to a prediction of a hypoglycemic event are established. Such conditional statements may be based on several processes. For example, a first process, e.g., prediction of a hypoglycemic event related to information based on current blood glucose values, and/or a second process, e.g., prediction of a hypoglycemic event related to a temperature-based prediction, and/or a third process, e.g., prediction of a hypoglycemic event related to a skin conductance-based prediction. A hypoglycemic event may be predicted by any or all of these processes (or one process combining all of these processes). This information is then coupled with information from, e.g., a fourth process, such as prediction of a hypoglycemic event based on a future value predicted by a time-series algorithm. The information from several or all of these processes may then be evaluated together. The more processes that predict a hypoglycemic event the more likely that prediction of a hypoglycemic event is correct. Accordingly, combining the predictions of these processes results in a more robust predictor of hypoglycemic events.

2.2 Description of an Exemplary Glucose Monitoring System

Numerous glucose monitoring systems can be used in the practice of the present invention. Typically, the monitoring system used to monitor the level of a selected glucose in a target system comprises a sampling device, which provides a sample comprising glucose, and a sensing device, which detects the amount or concentration of glucose or a signal associated with the glucose amount or concentration in the sample.

An exemplary glucose monitoring system which provides frequent measurements of glucose amount or concentrations is the GlucoWatch biographer system. This system is a wearable, non-invasive glucose monitoring system that provides a glucose reading automatically every twenty minutes. The GlucoWatch biographer system has several advantages including, but not limited to, the fact that its non-invasive and non-obtrusive nature encourages more frequent glucose testing among people (or animals) with diabetes. Of greater clinical relevance is the frequent nature of the information provided. Prior to the GlucoWatch biographer system no method existed for frequent glucose measurement outside of invasive means, often requiring hospital care (Mastrototaro, J. J., and Gross, T. M., "Clinical Results from the MiniMed Continuous Glucose Monitoring System" Proc. $31^{st}$ Annual Oak Ridge Conference, April, 1999). The GlucoWatch biographer system provides more frequent monitoring often desired by physicians in an automatic, non-invasive, and user-friendly manner. The automatic nature of the system also allows monitoring to continue even while a user is sleeping or otherwise unable to test.

The GlucoWatch biographer system comprises: (a) iontophoretic transport of glucose across the skin to non-invasively sample the glucose, (b) an electrochemical biosensor to measure the glucose concentration, and (c) an intelligent data-processing algorithm that coverts the raw biosensor signals to glucose readings while safeguarding against erroneous results through data point screening routines. These aspects of the system are briefly described below and are described more extensively in the publications referenced in the "Definitions" section, above.

The first aspect of the system is the iontophoretic extraction of glucose. Many small molecules are transported through the skin by either passive or facilitated means. Passive transport of compounds such as nicotine, estradiol, testosterone, etc. is the basis of transdermal drug delivery (skin patches). Transport through human skin can be greatly enhanced by the application of an electric field gradient. The use of a low-level electric current to enhance transport is known, generically, as iontophoresis.

Iontophoretic transport through skin can occur in either direction (Glikfeld, P., et al., Pharm. Res. 6, 988–990 (1989)). In particular, it was shown that small molecules such as glucose, ethanol, and theophylline are readily transported through the skin into an external collection chamber. Because transport through the skin is in the opposite direction to that used in iontophoretic drug delivery, this effect was described as "reverse iontophoresis" (U.S. Pat. No. 5,362,307, issued Nov. 8, 1994.; U.S. Pat. No. 5,279,543, issued Jan. 18, 1994.; U.S. Pat. No. 5,730,714, issued Mar. 24, 1998). In fact, because glucose is an uncharged molecule, transport is achieved through electro-osmosis. Results obtained from analyses using the GlucoWatch biographer system showed that extracted glucose correlated closely with blood glucose (Tamada, J. A., et al., JAMA 282:1839–1844, 1999).

The second aspect of the system involves the use of an electrochemical glucose biosensor. The GlucoWatch biographer system utilizes an electrochemical biosensor assembly to quantitate the glucose extracted through the skin. There are two biosensors in the GlucoWatch biographer system (FIG. 1). Each biosensor consists of a hydrogel pad containing the enzyme glucose oxidase (GOx) and a set of electrodes. One surface of the hydrogel pad contacts the skin while the opposite surface is in contact with the biosensor and iontophoresis electrodes. The hydrogel pads serve two functions. During iontophoresis the pads serve as the electrical contacts with the skin and the collection reservoirs for the extracted glucose. During the sensing portion of the cycle, the glucose extracted through the skin reacts with the GOx in the hydrogel pads via the reaction:

$$\text{Glucose} + O_2 \xrightarrow{GOx} \text{Gluconic acid} + H_2O_2.$$

The $H_2O_2$ produced by this reaction is then detected amperometrically at the platinum/carbon working electrode of the sensor. The integrated sensor current measured is proportional to the concentration of $H_2O_2$, and ultimately to the amount of glucose extracted. The extraction and sensing portions of the cycle occur in succession, and the cycle repeats to provide a measurement of glucose every twenty minutes.

For convenience to the user, the GlucoWatch biographer system was developed as a miniaturized device which can be worn on the wrist, forearm, upperarm, or other body part. The GlucoWatch biographer system durable component contains electronics for the biosensors and iontophoresis, a microprocessor, data storage memory, and an LCD display. Two sets of biosensors and iontophoresis electrodes are fitted onto the skin side of the device (e.g., a consumable component, the AutoSensor). A schematic diagram of the AutoSensor of the GlucoWatch biographer system is shown in FIG. 1.

Referring to FIG. 1, an exploded view of exemplary components comprising one embodiment of an AutoSensor for use in an iontophoretic sampling system is presented. The AutoSensor components include two biosensor/iontophoretic electrode assemblies, 104 and 106, each of which have an annular iontophoretic electrode, respectively indicated at 108 and 110, which encircles a biosensor electrode 112 and 114. The electrode assemblies 104 and 106 are printed onto a polymeric substrate 116 which is maintained within a sensor tray 118. A collection reservoir assembly 120 is arranged over the electrode assemblies, wherein the collection reservoir assembly comprises two hydrogel inserts 122 and 124 retained by a gel retaining layer 126 and mask layer 128. Further release liners may be included in the assembly, for example, a patient liner 130, and a plow-fold liner 132. In one embodiment, the electrode assemblies comprise bimodal electrodes. A mask layer 128 (for example, as described in PCT Publication No. WO 97/10356, published 20 Mar. 1997, and U.S. Pat. Nos. 5,735,273, 5,827,183, 6,141,573, and 6,201,979, all herein incorporated by reference) may be present. Other AutoSensor embodiments are described in WO 99/58190, published 18 Nov. 1999, herein incorporated by reference.

The mask and retaining layers are preferably composed of materials that are substantially impermeable to the analyte (e.g., glucose) to be detected (see, for example, U.S. Pat. Nos. 5,735,273, and 5,827,183, both herein incorporated by reference). By "substantially impermeable" is meant that the material reduces or eliminates analyte transport (e.g., by diffusion). The material can allow for a low level of analyte transport, with the proviso that the analyte that passes through the material does not cause significant edge effects at the sensing electrode used in conjunction with the mask and retaining layers. Examples of materials that can be used to form the layers include, but are not limited to, polyester, polyester derivatives, other polyester-like materials, polyurethane, polyurethane derivatives and other polyurethane-like materials.

The components shown in exploded view in FIG. 1 are for use in a automatic sampling system which is configured to be worn like an ordinary wristwatch, as described, for example, in PCT Publication No. WO 96/00110, published 4 Jan. 1996, herein incorporated by reference. The wristwatch housing can further include suitable electronics (e.g., one or more microprocessor(s), memory, display and other circuit components) and power sources for operating the automatic sampling system. The one or more microprocessors may control a variety of functions, including, but not limited to, control of a sampling device, a sensing device, aspects of the measurement cycle (for example, timing of sampling and sensing, and alternating polarity between electrodes), connectivity, computational methods, different aspects of data manipulation (for example, acquisition, recording, recalling, comparing, and reporting), etc.

The third aspect of the system is an intelligent data-processing algorithm that coverts the raw biosensor signals to glucose readings while safeguarding against erroneous results through data point screening routines. The raw current data obtained from the biosensors must be converted into an equivalent blood glucose value. Equations to perform this data conversion have been developed, optimized, and validated on a large data set consisting of GlucoWatch biographer and reference blood glucose readings from clinical trials on diabetic subjects (see, for example, WO 018289A1, published 6 Apr. 2000). This data conversion algorithm is programmed into a dedicated microprocessor in the GlucoWatch biographer system. The software also contains screens to exclude spurious data points that do not conform to objective, a priori criteria (e.g., data which contain noise above a certain threshold). Exemplary signal processing applications include, but are not limited to, those taught in the following U.S. Pat. Nos. 6,144,869, 6,233,471, 6,180,416, herein incorporated by reference.

In addition to the two glucose biosensors, the GlucoWatch biographer system also contains a temperature sensor and a skin conductivity sensor. Input from the former is used to exclude data points obtained during large thermal excursions. The skin conductivity input is used to exclude data obtained when the subject is perspiring profusely, as sweat contains glucose which may confound the value obtained for the extracted sample. Hence, these various screens reject data points that may provide false glucose information. The remaining data points are then suitable for clinical use.

The GlucoWatch biographer system is housed in a plastic case held in place, typically on the arm, with a wrist band. A single AAA battery is used as the primary power source with an additional back-up battery. The GlucoWatch biographer circuitry includes a microprocessor and a custom application specific integrated circuit (ASIC) chip containing the circuitry to run both the iontophoresis and biosensor functions. There is sufficient memory to store up to 4000 glucose readings which represents approximately three months of data with daily use. An LCD display and four push buttons on the face of the GlucoWatch biographer system comprise the user interface, and allow the user to control and customize the functions of the monitor as well as to display clock time and date, glucose readings, and GlucoWatch biographer operation status. Data can also be downloaded to a PC via a serial interface adapter.

Included in the software control is the ability for the user to select high and low glucose alert levels. If the GlucoWatch biographer system measures a glucose value outside of these alert levels, an alarm sounds to notify the user of the situation.

The disposable portion of the GlucoWatch biographer system is the AutoSensor, which contains the two sets of biosensor and iontophoresis electrodes and the corresponding hydrogel discs housed held in a pre-aligned arrangement by a mask layer. The AutoSensor snaps into the skin-side of the GlucoWatch biographer system to make the necessary electrical connections between the two portions.

The GlucoWatch biographer system also contains a thermistor to measure skin temperature, and a set of conductivity probes which rest on the surface of the skin to measure skin conductivity, a measure of perspiration. As described above, the temperature and sweat data are used in the present device to ensure that the biosensor data has not been affected by large temperature excursions or perspiration during the reading period.

In another embodiment of a monitoring system, the sampling/sensing mechanism and user interface may be found on separate components (e.g., WO 00/47109, published 17 Aug. 2000). Thus, the monitoring system can comprise at least two components, in which a first component comprises sampling mechanism and sensing mechanism that are used to extract and detect an analyte, for example, glucose, and a second component that receives the analyte data from the first component, conducts data processing on the analyte data to determine an analyte concentration and then displays the analyte concentration data. Typically, microprocessor functions (e.g., control of a sampling device, a sensing device, aspects of the measurement cycle, computational methods, different aspects of data manipulation or recording, etc.) are found in both components. Alternatively, microprocessing components may be located in one or the other of the at least two components. The second component of the monitoring system can assume many forms, including, but not limited to, the following: a watch, a credit card-shaped device (e.g., a "smart card" or "universal card" having a built-in microprocessor as described for example in U.S. Pat. No. 5,892,661, herein incorporated by reference), a pager-like device, cell phone-like device, or other such device that communicates information to the user visually, audibly, or kinesthetically.

Further, additional components may be added to the system, for example, a third component comprising a display of analyte values or an alarm related to analyte concentration, may be employed. In certain embodiments, a delivery unit is included in the system. An exemplary delivery unit is an insulin delivery unit. Insulin delivery units, both implantable and external, are known in the art and described, for example, in U.S. Pat. Nos. 5,995,860; 5,112,614 and 5,062,841, herein incorporated by reference. Preferably, when included as a component of the present invention, the delivery unit is in communication (e.g., wire-like or wireless communication) with the extracting and/or sensing mechanism such that the sensing mechanism can control the insulin pump and regulate delivery of a suitable amount of insulin to the subject.

Advantages of separating the first component (e.g., including the biosensor and iontophoresis functions) from the second component (e.g., including some microprocessor and display functions) include greater flexibility, discretion, privacy and convenience to the user. Having a small and lightweight measurement unit allows placement of the two components of the system on a wider range of body sites, for example, the first component may be placed on the abdomen or upper arm. This wider range of placement options may improve the accuracy through optimal extraction site selection (e.g., torso rather than extremities) and greater temperature stability (e.g., via the insulating effects of clothing). Thus, the collection and sensing assembly will be able to be placed on a greater range of body sites. Similarly, a smaller and less obtrusive microprocessor and display unit (the second component) provides a convenient and discrete system by which to monitor analytes. The biosensor readouts and control signals will be relayed via wire-like or wireless technology between the collection and sensing assembly and the display unit which could take the form of a small watch, a pager, or a credit card-sized device. This system also provides the ability to relay an alert message or signal during nighttime use, for example, to a site remote from the subject being monitored.

In one embodiment, the two components of the device can be in operative communication via a wire or cable-like connection. Operative communications between the components can be wireless link, i.e. provided by a "virtual cable," for example, a telemetry link. This wireless link can be uni- or bi-directional between the two components. In the case of more than two components, links can be a combination of wire-like and wireless.

2.3 Monitoring of Glucose Levels

To evaluate the usefulness of the GlucoWatch biographer system in the monitoring of glucose levels, more than 90 subjects with diabetes were enrolled at three clinical sites around the United States. Subjects wore a GlucoWatch biographer system on their wrist for 15 hours while in a clinical setting. Subjects entered the clinic early in the morning in a fasted state. The GlucoWatch biographer system was applied and a "warm-up" procedure of 175 minutes was initiated. At the end of the warm-up period, the subjects took a single finger-stick blood glucose measurement which they used to calibrate the GlucoWatch biographer readings. From that point on, the GlucoWatch biographer system took three measurements per hour for the remainder of the study. All data were stored internally (i.e., in the biographer's memory). In addition, two standard blood measurements were obtained at 0 and 40 minutes during each hour. Thus, there were as many as 36 Gluco-Watch biographer data points and 24 matching blood data points obtained from each subject.

Figure 2:
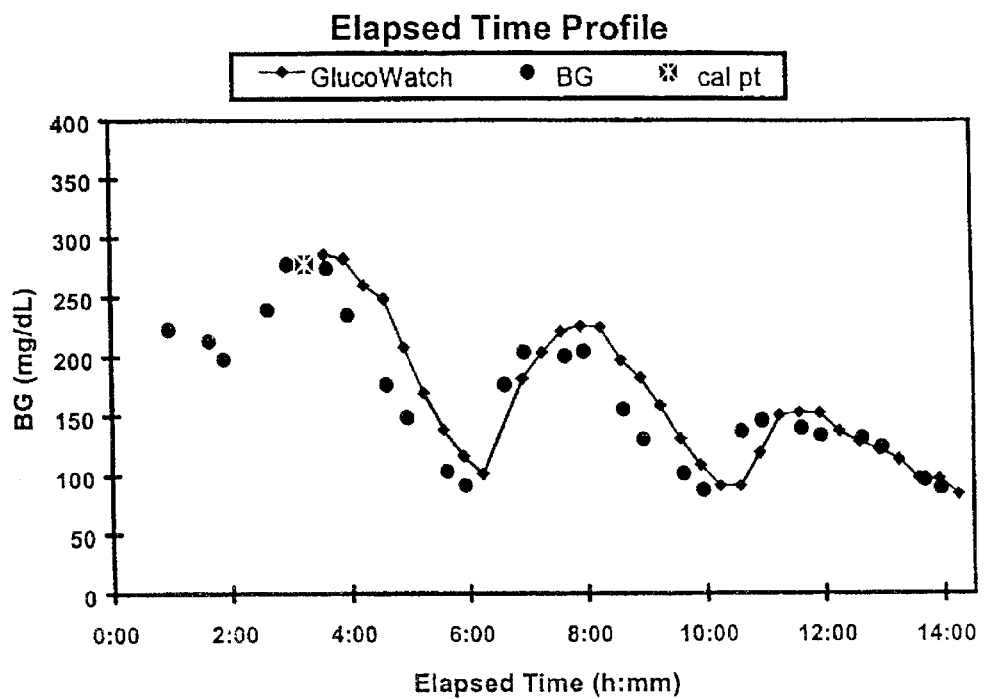
FIG. 2 presents a comparison of GlucoWatch biographer measurement with conventional blood glucose measurement over 14 hours for one subject.

The GlucoWatch biographer readings and blood data were then transferred into a computer for algorithm development and subsequent data analysis. The data were randomly divided into two groups. The data from one part of the data set (46 GlucoWatch biographer systems) were used to "train" the algorithm (the Mixtures of Experts algorithm, see, for example, WO 018289A1, published 6 Apr. 2000), that is, to determine the optimal functional form and parameter set needed to minimize the error between the GlucoWatch biographer system-predicted glucose values and blood glucose values. The optimized algorithm was then used to predict the GlucoWatch biographer system values for all subsequent data. This "out of sample" prediction technique diminished bias and demonstrated the universal nature of the algorithm. Data from one individual is shown in FIG. 2.

The result of this analysis for the 109 GlucoWatch biographer systems in the "out of sample" test group showed a time-delay of about 15 minutes between the extracted glucose relative to the blood glucose. Using the paired Gluco-Watch biographer measurement-blood measurement data, an average correlation coefficient of 0.88 was obtained, and 97% of the results fell in the clinically acceptable regions of the Clarke Error Grid Analysis (Clarke, W. L., et al., Diabetes Care 10:622–628 (1987)). In addition, the mean absolute error was 15.6%. Less than 8% of the data were removed by the "temperature", "sweat" and "noise" data integrity screens. These and other statistical analyses suggested that the GlucoWatch biographer system is comparable to commercially available blood monitoring devices over a broad range of values (40 to 400 mg/dL in these studies).

The clinical results cited above clearly demonstrate that the GlucoWatch biographer system tracks glucose in human subjects with diabetes.

2.4 Temperature and Perspiration as Indicators of Hypoglycemia

Preliminary tests of the correlation between skin temperature and skin conductivity, and hypoglycemic blood glucose levels were performed on data from one clinical trial. Temperature and perspiration data from the GlucoWatch biographer system were analyzed for a total of 213 GlucoWatch biographer system applications on 121 diabetic subjects. This data set consists of the temperature, perspiration measurement and reference blood glucose value for 5346 GlucoWatch biographer measurement cycles. For this trial, the subjects were tested in a clinical setting, but were allowed general freedoms simulating a home environment.

Figure 3:
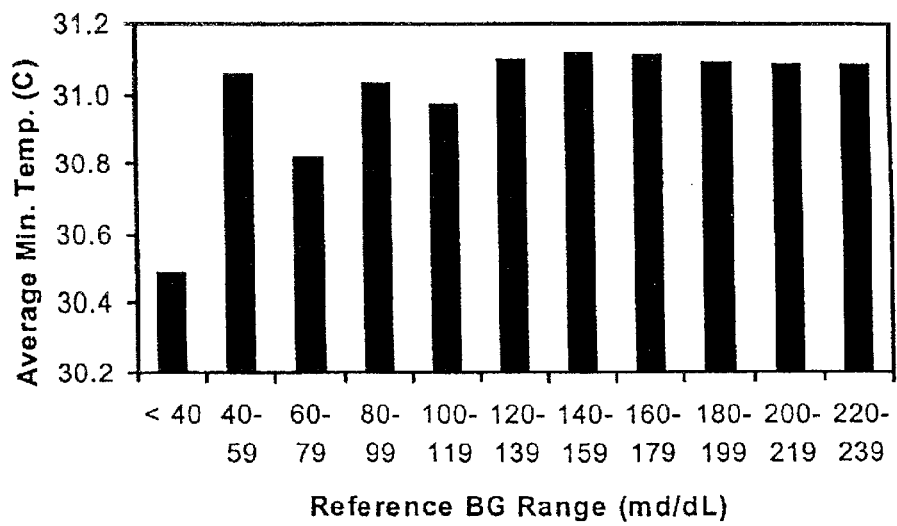
FIG. 3 presents data showing the average minimum temperature during each GlucoWatch biographer measurement cycle vs. reference blood glucose.

In order to determine whether a correlation existed between skin temperature and perspiration, and hypoglycemia, the data were sorted into reference blood glucose range bins from <40 mg/dL to 240 mg/dL. The minimum skin temperature for each measurement cycle in each bin was averaged and plotted in FIG. 3. As can be seen from the results presented in the figure, the skin temperature as measured by the GlucoWatch biographer system is lower than average when the reference blood glucose is lower than 120 mg/dL, and is lowest when the blood glucose is in the lowest hypoglycemic range. This preliminary result demonstrated a correlation between lower average skin temperature and hypoglycemic blood glucose levels.

Accordingly, in one aspect of the present invention, one of the parameters that may be used for the prediction of a hypoglycemic event is a below average skin temperature. Ideally, an average skin temperature is determined for each subject by collecting a skin temperature reading data set over an extended period of time (e.g., days, weeks, or months). An associated standard deviation and/or average variation may be associated with the average skin temperature using standard statistical methods applied to the skin temperature reading data set. The average temperature may also be associated with the time of day, for example, the day broken down into 1–8 hour increments (including all time values in the range, e.g., 2.5 hours) in order to account for normal skin temperature variations associated, for example, with a mid-day time period and a sleep time period. Such associations may be established employing standard statistical manipulations, such as trend analysis or multivariate analysis of variance. Further, using trend analysis or the TSES equation described herein, based on a series of skin temperature readings, a skin temperature reading at a future time point could be predicted or extrapolated. In one aspect of the present invention, the skin temperature reading parameter, when below average body temperature for the subject, is an indicator of a possible hypoglycemic event. As noted above, a standard deviation (and/or variance) may be associated with the average body temperature of the subject to provide a reference range. When the body temperature of the subject falls below such a reference range (taking into account statistical variation, such as standard deviation), that is an indicator of a possible hypoglycemic event. For example, for the cumulative data presented in FIG. 3, such a reference range may be 31° C.±0.05° C. (or more generally stated, average body temperature of the subject plus/minus the standard deviation or variance associated with the average body temperature). Confidence intervals may also be used to establish such ranges.

Similarly, if a decreasing body temperature trend is detected (for example, using a regression analysis or other trend analysis) such a trend of decreasing body temperature may be used as an indicator of a hypoglycemic event.

In another aspect, fluctuations of body temperature may be used as an indicator of a hypoglycemic event: for example, such fluctuations may be determined relative to a reference range.

Figure 4:
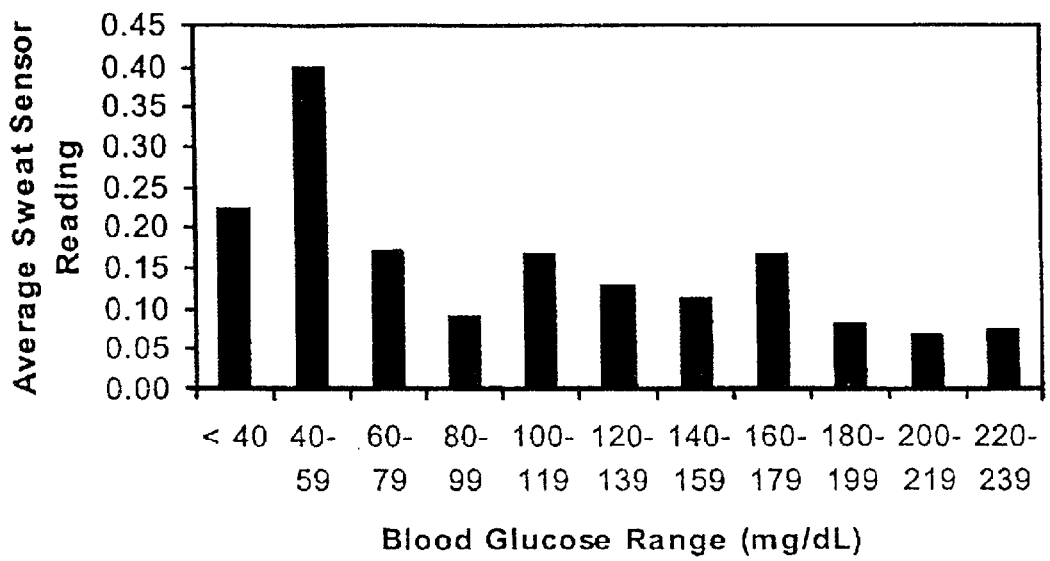
FIG. 4 presents data showing average skin conductivity reading vs. blood glucose range.

The data from the skin conductivity sensor on the GlucoWatch biographer system was plotted in a similar manner. The GlucoWatch biographer skin conductivity measurement was converted to an arbitrary scale from 0–10. For data integrity screening purposes, skin conductivity readings above 1 were considered an indication of perspiration occurring. FIG. 4 shows the average skin conductivity reading for all the measurement cycles within each reference blood glucose range. The trend was relatively flat over the euglycemic and hyperglycemic ranges with the three highest averages occuring in the <40 mg/dL, 40–59 mg/dL, and 60–79 mg/dL ranges in the hypoglycemic region, indicating a higher degree of perspiration in the hypoglycemic region.

Figure 5:
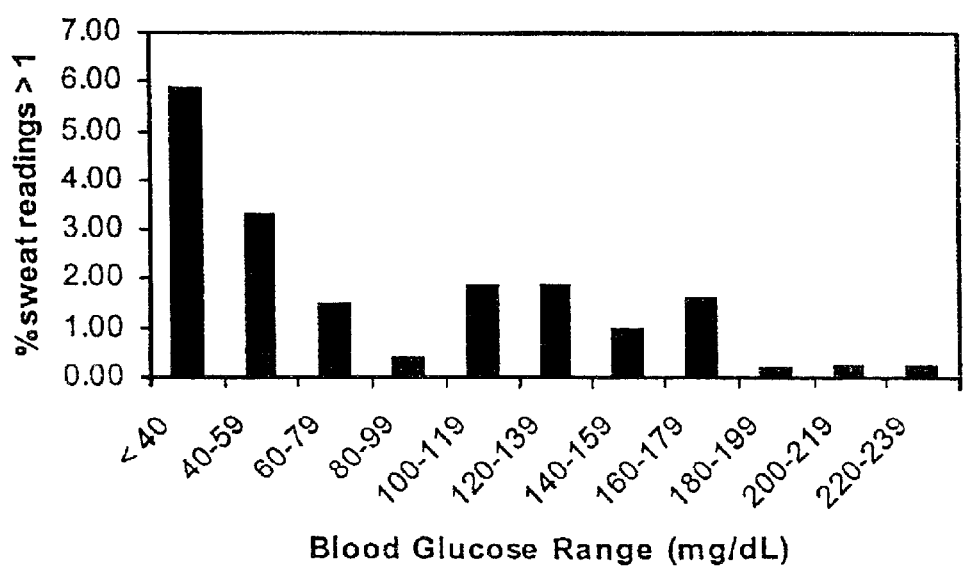
FIG. 5 presents data showing percentage of skin conductivity readings indicating perspiration vs. blood glucose range.

The data shown in FIG. 4 was presented in a different manner by taking the percentage of all readings with skin conductivity readings greater than one (therefore, above the a priori determined perspiration threshold) and plotting them with reference to the same reference blood glucose ranges (see FIG. 5). The data presented in FIG. 5 showed pronounced increase in the percentage of positive perspiration indications in the hypoglycemic regions below 60 mg/dL.

Accordingly, in one aspect of the present invention, one of the parameters that may be used for the prediction of a hypoglycemic event is an above or below average sweat sensor reading (i.e., skin conductance). In one embodiment of the present invention, skin conductance above a predetermined perspiration threshold (or range) is a predictor of a hypoglycemic event (see, for example, reference data in FIGS. 4 and 5). Ideally an average skin conductance reading is determined for each subject by collecting a skin conductance reading data set over an extended period of time (e.g., days, weeks, or months). An associated standard deviation and/or average variation may be associated with the average skin conductance using standard statistical methods applied to the skin conductance reading data set. The average skin conductance may also be associated with the time of day; for example, the day broken down into 1–8 hour increments (including all time values in the range, e.g., 2.5 hours) in order to account for normal skin conductance variations associated, for example, with a mid-day time interval and a sleep interval. Such associations may be established employing standard statistical manipulations, such as trend analysis or multivariate analysis of variance. Further, using trend analysis or the TSES equation described herein, based on a series of skin conductance readings, a skin temperature reading at a future time point could be predicted or extrapolated. In one aspect of the present invention, the skin conductance reading parameter, when above or below average skin conductance for the subject, is an indicator of a possible hypoglycemic event. As noted above, a standard deviation (and/or variance) may be associated with the average skin conductance of the subject to provide a reference range. When the skin conductance of the subject falls outside of such a reference range (taking into account statistical variation, such as standard deviation), that is an indicator of a possible hypoglycemic event. For example, for the cumulative data presented in FIG. 4, such a reference range may a skin conductance reading of 0.15±0.025 average sweat sensor reading (or more generally stated, average skin conductance of the subject plus/minus the standard deviation or variance associated with the average skin conductance). Confidence intervals may also be used to establish such ranges.

Similarly, if an increasing or decreasing skin conductance trend is detected (for example, using a regression analysis or other trend analysis) such a trend of increasing or decreasing skin conductance may be used as an indicator of a hypoglycemic event.

In another aspect, fluctuations of skin conductance may be used as an indicator of a hypoglycemic event: for example, such fluctuation can be determined relative to a reference range.

Body temperature (or body temperature trends) and/or skin conductance (or skin conductance trends) can be used together or singly as parameters useful for the prediction of a hypoglycemic event. Typically, use of such a parameter is coupled with the time series forecasting method described below.

Threshold values (or ranges of values) for selected parameters may be employed in the prediction of hypoglycemic events. Such threshold values can be established, for example, based on review and analysis of a record of the subject's glucose values, body temperature and skin conductance. A statistical program can be used to provide correlations between known hypoglycemic events (from the subject's record, which is created using a glucose monitoring device capable of providing frequent glucose, temperature, and skin conductance readings) and the selected parameters. Such statistical programs are known in the art and include, for example, decision tree and ROC analysis (see below).

2.5 Time Series Forecasting

Time-series forecasting, the prediction of future values of a variable from past observations, is a procedure used for extrapolation of data series. There are a number of methods that may be used for time-series forecasting, including, but not limited to, the following: extrapolation of linear or polynomial regression, autoregressive moving average, and exponential smoothing.

A method for time-series forecasting, called Taylor Series Exponential Smoothing (TSES) has been developed and was disclosed in co-owned, co-pending WO 99/58973, published 18 Nov. 1999. In one embodiment, this method utilized the data points from the previous 60 minutes, as well as the associated first and second derivative values to predict the value of the next data point. The method of exponential smoothing calculates the predicted value of a variable y at time n+1 as a function of that variable at the current time n, as well as at two previous times n−1 and n−2. The equation that is typically used for the case of evenly spaced time points is shown as equation (1) below.

$$y_{n+1} = \beta y_n + \beta(1-\beta)y_{n-1} + \beta(1-\beta)^2 y_{n-2} \quad (1)$$

In this equation, β is an empirical parameter obtained from experimental data which is typically between 0 and 1.

An improvement to equation (1) is as follows: First, there is a resemblance between equation 1 and a Taylor Series expansion, shown as equation (2).

$$f(x) = f(a) + f'(a)(x-a) + \frac{f''(a)(x-a)^2}{2!} + \ldots + \frac{f^{(n-1)}(a)(x-a)^{(n-1)}}{(n-1)!} \quad (2)$$

Accordingly, the variable $y_{n-1}$ was replaced by $y_n'$ (the first derivative at $y_n$ with respect to time) and $y_{n-2}$ was replaced by $$\frac{y_n''}{2}$$

(the second derivative at $y_n$ with respect to time) to give equation (3), $$y_{n+1} = \beta y_n + \beta(1-\beta)y_n' + \frac{\beta(1-\beta)^2}{2}y_n'' \quad (3)$$

where the derivatives are calculated by the following two equations:

$$y_n' = \frac{y_n - y_{n-1}}{\Delta t} \quad (4)$$

$$y_n'' = \frac{y_n - 2y_{n-1} + y_{n-2}}{\Delta t} \quad (5)$$

and Δt is the equally spaced time interval.

The analogy between equation (3) and the Taylor Series, equation (2), can be further improved by dividing the right hand side of equation (3) by β to give equation (6) where the definition α=1−β is used.

$$y_{n+1} = y_n + \alpha y_n' + \frac{\alpha^2}{2}y_n'' \quad (6)$$

Substituting equations (4) and (5) into equation (6), gives the final expression of the Taylor Series Exponential Smoothing (TSES) equation as:

$$y_{n+1} = y_n + \alpha(y_n - y_{n-1}) + \frac{\alpha^2}{2}(y_n - 2y_{n-1} + y_{n-2}) \quad (7)$$

The TSES equation is essentially an exponentially smoothed moving average Taylor series expansion using the first two terms of the Taylor series. This technique may be adapted to work with the measurements produced by the GlucoWatch biographer system to predict glucose levels at least one measurement cycle ahead (WO 99/58973, published 18 Nov. 1999, herein incorporated by reference in its entirety).

2.6 Improved Prediction of Hypoglycemic Events

The present invention comprises methods for the improved ability to predict hypoglycemia which include a two-fold approach. First, additional physiological data, namely skin temperature and skin conductivity, are used in combination with frequent glucose value readings (obtained, for example, using the GlucoWatch biographer system) to produce a more robust prediction algorithm than may be achieved by using any of the variables alone. Second, a time-series forecasting technique is used in conjunction with a data stream comprising frequent glucose measurements (obtained, for example, using the GlucoWatch biographer system) to predict future glucose levels and provide an early warning of incipient hypoglycemic events. The synergy of these two different approaches provides an improved ability to predict hypoglycemia events.

2.7 Incorporation of Sweat and Temperature Measurements into a Hypoglycemia Prediction Algorithm A data set consisting of approximately 16,000 pairs of GlucoWatch biographer data and reference blood glucose values for approximately 450 diabetic patients has been generated in support of the present invention. Both Type 1 and Type 2 diabetics with a wide variety of demographic backgrounds are represented in this data set. The data set may be used as a test bed for developing and refining the incorporation of the skin temperature and conductivity readings into a hypoglycemia predictive algorithm. The data set is sufficiently large to enable a hypoglycemia predictive algorithm to be trained on a randomized subset of data, and tested on a separate "out of sample" subset. Using this set of raw data, GlucoWatch biographer system outputs can be produced using an emulator program which completely mimics the device operation. The skin temperature and conductivity readings are incorporated into a hypoglycemia alert function in the emulator, and the simulated results (glucose readings, occurrence of hypoglycemia alert soundings, etc.) are recorded and predictive efficacy evaluated.

A number of different functions are evaluated for their ability to correctly predict hypoglycemia using the skin temperature, skin conductivity, and glucose data. The preliminary data presented in FIGS. 3–5 and described above represent the simplest of these functions, that is, use of the discrete data points at each GlucoWatch biographer measurement cycle. More complex algorithms may utilize, for example, variation of the temperature and conductivity parameters from a sliding average baseline value, monitoring of trends in these parameters, or more complex neural network approaches.

Numerous suitable estimation techniques useful in the practice of the invention are known in the art. These techniques may be used to provide correlation factors (e.g., constants), which correlation factors are then used in a mathematical transformation to obtain a measurement value indicative of a hypoglycemic event. In particular embodiments, the hypoglycemic predictive algorithm may apply mathematical, statistical and/or pattern recognition techniques to the problem of signal processing in chemical analyses, for example, using neural networks, genetic algorithm signal processing, linear regression, multiple-linear regression, principal components analysis of statistical (test) measurements, decision trees, or combinations thereof. The structure of a particular neural network algorithm used in the practice of the invention may vary widely; however, the network may, for example, contain an input layer, one or more hidden layers, and one output layer. Such networks can be trained on a test data set, and then applied to a population. There are many suitable network types, transfer functions, training criteria, testing and application methods which will occur to the ordinarily skilled artisan upon reading the instant specification. One such evaluation method is a Mixtures of Experts algorithm (see, for example, WO 018289A1, published 6 Apr. 2000; U.S. Pat. No. 6,180,416, issued 30 Jan. 2001, herein incorporated by reference in its entirety). In a Mixtures of Experts algorithm, skin conductance and/or body temperatures can be included as parameters to provide more accurate prediction of blood glucose and, in particular, more accurate prediction of potential hypoglycemic events.

One method to evaluate the effectiveness of a proposed hypoglycemia alert function examines each set of paired GlucoWatch biographer/reference blood points to determine whether the hypoglycemia alert function correctly predicted the presence or absence of hypoglycemia. The number of false positives (prediction of hypoglycemia when none existed) or false negatives (missing hypoglycemia when it did exist) is tabulated and used to calculate the sensitivity and specificity of the alert function.

A second analysis anticipates that each hypoglycemic episode can be predicted by several readings in the continual data stream of the GlucoWatch biographer system. For such an analysis, the number of hypoglycemic events predicted (and not predicted) by the hypoglycemia alert function of GlucoWatch biographer system is tabulated and used to calculate the predictive value of the hypoglycemia alert function. Using such approaches the hypoglycemia alert function is optimized on a pre-existing data set and is then tested in clinical trials on diabetic patients.

Accordingly, the incorporation of data from the sweat and temperature probes into the glucose-level prediction algorithm is tested using the existing clinical database. Optimization of the algorithm parameters is performed to minimize error in the glucose readings and maximize the accuracy of the hypoglycemia alarm function.

2.8 Time-Series Forecasting Algorithm

The GlucoWatch biographer system's ability to acquire glucose data on a frequent basis creates a large database heretofore unavailable to a patient or clinician. The time-series forecasting algorithm described above uses a series of closely spaced glucose readings to "forecast" a future reading. This algorithm provides an early warning of incipient hypoglycemic events, the most serious acute complication for diabetics.

An adaptive neural network technology may be combined with this time forecasting concept to provide a system that is customized to an individual patient's physiology. This process involves training the neural network with a sufficient number of paired monitor and reference blood glucose values from a given patient. In this way, the neural network "learns" the patterns in an individual's blood glucose changes. This approach reduces error in the prediction of hypoglycemia events.

Optimization of forecasting algorithms is carried out using the "data mining" approach essentially as described above to investigate the skin temperature-conductivity data. The time-series forecasting algorithms are trained and tested on the data set of GlucoWatch biographer system values and corresponding blood glucose reference values obtained during clinical trials and described above. Various statistical measures of accuracy are used to evaluate and optimize forecasting algorithms including difference statistics (mean error, mean relative error, mean absolute error), RMS error, and the Clarke Error Grid Analysis. The optimized forecasting algorithm is then prospectively tested in clinical trials essentially as follows.

Initial clinical trials are conducted with non-diabetic volunteers in order to verify that the modified GlucoWatch biographer systems function properly. Such trials also provide an early assessment of the capabilities of the hypoglycemia alert function. The clinical protocol is essentially performed as follows. A 100 gram oral glucose tolerance test (OGTT) has historically predicted device performance in a population of subjects with diabetes. In addition, following OGTT, after the glucose peak, non-diabetic subjects can achieve blood glucose levels as low as 50–70 mg/dL from endogenous insulin production, thus providing data to test the prediction of hypoglycemia. Moreover, since one subject may wear multiple GlucoWatch biographer systems, meaningful data may be obtained with as few as 10 subjects.

Following trials with non-diabetic subjects, the modified GlucoWatch biographer system comprising an improved hypoglycemic alert function is tested on subjects with diabetes. Typically, results from a minimum of 20 subjects over at least five consecutive days are used to generate data sufficient to develop and optimize the algorithms. The demographic profile of the subjects included in these clinical trials is diverse, as it is beneficial to investigate performance on as wide a demographic sample as possible. These trials typically study subjects with both Type 1 and Type 2 in relatively equal numbers. Male and female subjects are represented fairly evenly. The subject population has a wide range of ages. The ethnic background of a typical large clinical trial is shown below in Table 1 as an example where 120 of the subjects are female and 111 were male. Typically the test population comprises subjects 18 years or older.

TABLE 1

| American Indian or Alaskan Native | Asian or Pacific Islander | Black, not of Hispanic Origin | Hispanic | White, not of Hispanic Origin | Other or Unknown | Total |
|---|---|---|---|---|---|---|
| 1 | 1 | 24 | 36 | 166 | 3 | 231 |

The general design of the study day is as follows. The subjects arrive at the clinic in the morning having fasted from midnight the night before, and having not taken their morning insulin injection. Two GlucoWatch biographer systems are applied to the subject's arm, synchronized with clock time, and started. Over the course of the study (approximately 15 hours), capillary blood samples are obtained twice per hour, and measured with a reference method for comparison with the GlucoWatch biographer measurements. During the course of the measurement period, insulin dosing is adjusted by the investigator to achieve mildly hypoglycemic and hyperglycemic glucose levels. The targeted blood glucose range is 40–450 mg/dL. At the end of the 15 hour study, the GlucoWatch biographer systems are removed by laboratory personnel.

The data collected from each patient consists of demographic information, medical screening data, reference blood glucose measurements, and GlucoWatch biographer system measurements. These data are used for the purposes of evaluating the hypoglycemic prediction algorithm.

Accordingly, the optimum time-series algorithm model and variables to be used in the model are determined by "training" and testing on a large database of clinical GlucoWatch biographer system data. The algorithm is optimized to minimize error in the glucose readings and maximize the accuracy of the hypoglycemia alarm function. This optimized time-series prediction model is combined with one or more predictions of hypoglycemic events, e.g., using a sweat and temperature probe based predictive algorithm, as described above. The hypoglycemic predictive approach described herein utilizes information obtained from a data stream, e.g., frequently obtained glucose values, skin conductance or temperature readings, generated by a frequent sampling glucose monitoring device, e.g., the GlucoWatch biographer system, coupled with a time-series forecasting approach, to predict incipient hypoglycemic events and to alert the user.

One or more microprocessors may be used to coordinate the functions of the sampling device, sensing device, and predictive algorithms. Such a microprocessor generally uses a series of program sequences to control the operations of the sampling device, which program sequences can be stored in the microprocessor's read only memory (ROM). Embedded software (firmware) controls activation of measurement and display operations, calibration of analyte readings, setting and display of high and low analyte value alarms, display and setting of time and date functions, alarm time, and display of stored readings. Sensor signals obtained from the sensor electrodes can be processed before storage and display by one or more signal processing functions or algorithms which are stored in the embedded software. The microprocessor can also include an electronically erasable, programmable, read only memory (EEPROM) for storing calibration parameters, user settings and all downloadable sequences. A serial communications port may be used to, for example, allow the monitoring device to communicate with associated electronics, for example, wherein the device is used in a feedback control application to control a pump for delivery of a medicament such as insulin (using, e.g., an insulin pump).

Accordingly, one aspect of the present invention provides a method for predicting a hypoglycemic event in a subject. Typically, a threshold glucose value or range of glucose values is determined that corresponds to a hypoglycemic event. Symptom producing low plasma glucose levels vary in individuals and in different physiological states. Abnormally low plasma glucose is usually defined as less than or equal to about 50 mg/dL in men, about 45 mg/dL in women, and about 40 mg/dL in infants and children. The methods of the present invention for prediction of a hypoglycemic event are, generally, to avoid glucose levels dropping to such low levels in the subject. Accordingly, a threshold for a glucose measurement value indicative of a hypoglycemic event may be set higher (e.g., between about 80 to about 100 mg/dL) in order to give the subject more time to respond and prevent glucose levels from dropping into the hypoglycemic range. Further, at least one threshold parameter value (or range of values) that is correlated with a hypoglycemic event is also determined, for example where the parameter is skin conductance reading or body temperature reading.

A series of glucose measurement values at selected time intervals is obtained using a selected glucose sampling system (for example, the GlucoWatch biographer). Using the series of measurements, typically a series of at least three glucose measurement values, a glucose measurement value at a further time interval (e.g., n+1, where the last glucose measurement value of the series was n) subsequent to the series of measurement values is predicted. This predicted glucose measurement value can be obtained, for example, using the time series forecasting method described above. Other predictive algorithms may be used as well.

In addition, another parameter value or trend of parameter values is measured concurrently, simultaneously, or sequentially with the obtaining of the series of glucose measurement values. Skin conductance and body temperature are two preferred parameters. Either the parameter value (for example at time point n, or a predicted value for the parameter at a later time point, for example, n+1) or trend of parameter values are compared with a threshold parameter value (or range of values) to determine whether the measured parameter value or trend of parameter values is suggestive of a hypoglycemic event. A hypoglycemic event is predicted for the subject when both (i) comparing the predicted glucose measurement value to the threshold glucose value indicates a hypoglycemic event at time interval n+1, and (ii) comparing said parameter with said threshold parameter value indicates a hypoglycemic at time interval n or n+1. Typically one or more microprocessors are programmed to control data acquisition (e.g., the glucose measurement cycle and obtaining of skin conductance and/or body temperature readings) by being programmed to control devices capable of collecting the required data points. The one or more microprocessors also typically comprise programming for algorithms to control the various predictive and comparative methods.

2.9 Prediction of Hypoglycemic Events Using a Decision Tree Model

In one aspect of the present invention, the method for prediction of hypoglycemic events employs a decision tree (also called classification tree) which utilizes a hierarchical evaluation of thresholds (see, for example, J. J. Oliver, et. al, in Proceedings of the 5th Australian Joint Conference on Artificial Intelligence, pages 361–367, A. Adams and L. Sterling, editors, World Scientific, Singapore, 1992; D. J. Hand, et al., Pattern Recognition, 31(5):641–650, 1998; J. J. Oliver and D. J. Hand, Journal of Classification, 13:281–297, 1996; W. Buntine, Statistics and Computing, 2:63–73, 1992; L. Breiman, et al., "Classification and Regression Trees" Wadsworth, Belmont, Calif., 1984; C4.5: Programs for Machine Learning, J. Ross Quinlan, The Morgan Kaufmann Series in Machine Learning, Pat Langley, Series Editor, October 1992, ISBN 1-55860-238-0). Commercial software for structuring and execution of decision trees is available (e.g., CART (5), Salford Systems, San Diego, Calif.; C4.5 (6), RuleQuest Research Pty Ltd., St Ives NSW Australia; and Dgraph (1,3), Jon Oliver, Cygnus, Redwood City, Calif.) and may be used in the methods of the present invention in view of the teachings of the present specification. A simple version of such a decision tree is to choose a threshold current glucose value reading, a threshold body temperature value, and a threshold skin conductance (sweat) value. If a current (or predicted) glucose value reading is equal to or below the threshold glucose value, then the body temperature is evaluated. If the body temperature is below the threshold body temperature value, then skin conductance is evaluated. If skin conductance is greater than the threshold skin conductance value, then a hypoglycemic event is predicted.

For example, a first level decision is made by the algorithm based on the most recent glucose value obtained by the monitoring device compared to initial thresholds that may indicate a hypoglycemic event. For example, the algorithm may compare the current blood glucose value (time=n) or a predicted glucose value (time=n+1) to a threshold value (e.g., 100 mg/dL). If the glucose value is greater than the threshold value then a decision is made by the algorithm to continue monitoring. If the glucose level is less than or equal to the threshold glucose level then the algorithm continues with the next level of the decision tree.

The next level of the decision tree may be an evaluation of the subject's body temperature reading at time (n), which is compared to a threshold body temperature. For example, if the body temperature is greater than the threshold body temperature (e.g., 33.95° C. ) then a decision is made by the algorithm to continue monitoring. If the body temperature is less than or equal to the threshold the threshold body temperature (e.g., 33.95° C.) then the algorithm continues with the next level of the decision tree.

The next level of the decision tree may be an evaluation of the subject's skin conductance reading at time (n), which is compared to a threshold skin conductance. For example, if the skin conductance (i.e., sweat reading) is less than the threshold skin conductance (e.g., 0.137 sweat sensor reading) then a decision is made by the algorithm to continue monitoring. If the skin conductance is greater than or equal to the threshold skin conductance then the algorithm predicts a hypoglycemic event.

The decision tree could be further elaborated by adding further levels. For example, after a determination that a hypoglycemic event is possible the next glucose level can be evaluated to see if it is above or below the threshold value. Both body temperature and skin conductance could be tested as above once again to confirm the prediction of a hypoglycemic event.

The most important attribute is typically placed at the root of the decision tree. In one embodiment of the present invention the root attribute is the current glucose reading. In another embodiment, a predicted glucose reading at a future time point may be the root attribute. Alternatively, body temperature or skin conductance could be used as the root attribute.

Further, thresholds need not be established a priori. The algorithm can learn from a database record of an individual subject's glucose readings, body temperature, and skin conductance. The algorithm can train itself to establish threshold values based on the data in the database record using, for example, a decision tree algorithm.

Further, a decision tree may be more complicated than the simple scenario described above. For example, if skin conductance (i.e., sweat) is very high the algorithm may set a first threshold for the body temperature which is higher than normal, if the skin conductance reading is medium, the algorithm might set a relatively lower body temperature threshold, etc.

By selecting parameters (e.g., current or future glucose reading, body temperature, skin conductance) and allowing the algorithm to train itself based on a database record of these parameters for an individual subject, the algorithm can evaluate each parameter as independent or combined predictors of hypoglycemia. Thus, the hypoglycemia prediction model is being trained and the algorithm determines what parameters are the most important indicators. A decision tree may be learnt in an automated way from data using an algorithm such as a recursive partitioning algorithm. The recursive partitioning algorithm grows a tree by starting with all the training examples in the root node. The root node may be "split," for example, using a three-step process as follows. (1) The root node may be split on all the attributes available, at all the thresholds available (e.g., in a training database). To each considered split a criteria is applied (such as, GINI index, entropy of the data, or message length of the data). (2) An attribute (A) and a threshold (T) are selected which optimize the criteria. This results in a decision tree with one split node and two leaves. (3) Each example in the training database is associated with one of these two leaves (based on the measurements of the training example). Each leaf node is then recursively split using the three-step process. Splitting is continued until a stopping criteria is applied. An example of a stopping criteria is if a node has less than 50 examples from the training database that are associated with it.

In a further embodiment, at each level of the decision in the decision tree, the algorithm software can associate a probability with the decision. The probabilities at each level of decision can be evaluated (e.g., summed) and the cumulative probability can be used to determine whether to set off an alarm indicating a hypoglycemic event.

Receiver Operating Characteristic (ROC) curve analysis can be applied to decision tree analysis described above ROC analysis is another threshold optimization means. It provides a way to determine the optimal true positive fraction, while minimizing the false positive fraction. A ROC analysis can be used to compare two classification schemes, and determine which scheme is a better overall predictor of the selected event (e.g., a hypoglycemic event); for example, a ROC analysis can be used to compare a simple threshold classifier with a decision tree. ROC software packages typically include procedures for the following: correlated, continuously distributed as well as inherently categorical rating scale data; statistical comparison between two binormal ROC curves; maximum likelihood estimation of binormial ROC curves from set of continuous as well as categorical data; and analysis of statistical power for comparison of ROC curves. Commercial software for structuring and execution of ROC is available (e.g., Analyse-It for Microsoft Excel, Analyse-It Software, Ltd., Leeds LS12 5XA, England, UK; MedCalc®, MedCalc Software, Mariakerke, Belgium; AccuROC, Accumetric Corporation, Montreal, Quebec, Calif.).

Related techniques that can be applied to the above analyses include, but are not limited to, Decision Graphs, Decision Rules (also called Rules Induction), Discriminant Analysis (including Stepwise Discriminant Analysis), Logistic Regression, Nearest Neighbor Classification, Neural Networks, and Naive Bayes Classifier.

Although preferred embodiments of the subject invention have been described in some detail, it is understood that obvious variations can be made without departing from the spirit and the scope of the invention as defined by the appended claims.

What is claimed is:

1. A method for predicting a hypoglycemic event in a subject, said method comprising
    determining (i) a threshold glucose value that corresponds to said hypoglycemic event, and (ii) a threshold skin conductance and/or temperature value that is correlated with said hypoglycemic event;
    obtaining a series of glucose measurement values at selected time intervals using a method comprising
        obtaining a raw signal specifically related to a glucose amount or concentration in the subject for a given time interval,
        correlating the raw signal with a glucose measurement value indicative of the amount or concentration of glucose present in the subject in said given time interval,
        repeating said obtaining and correlating to provide a series of glucose measurement values at selected time intervals,
        predicting a glucose measurement value at a further time interval subsequent to said series of glucose measurement values, and
        comparing said predicted glucose measurement value to said threshold glucose value, wherein when the a predicted glucose measurement value is less than or equal to the threshold glucose value a hypoglycemic event is predicted;
    measuring skin conductance and/or temperature of the subject concurrently, simultaneously, or sequentially with said obtaining of the series of glucose measurement values, and comparing said skin conductance and/or temperature value or trend of skin conductance and/or temperature values with said threshold skin conductance and/or temperature value to determine whether said skin conductance and/or temperature value or trend of skin conductance and/or temperature values indicates a hypoglycemic event; and
    predicting a hypoglycemic event in said subject when both (i) comparing the predicted glucose measurement value to said threshold glucose value indicates a hypoglycemic event at said further time interval, and (ii) comparing said skin conductance and/or temperature value or trend of skin conductance and/or temperature values with said threshold skin conductance and/or temperature value indicates a hypoglycemic event.

2. The method of claim 1, wherein said obtaining of the series of glucose measurement values is performed using a near-IR spectrometer.

3. The method of claim 1, wherein the values or trend of values for both skin conductance readings and temperature readings are used to predict the likelihood of a hypoglycemic event.

4. The method of claim 1, wherein the selected time intervals are evenly spaced.

5. The method of claim 1, wherein the series of glucose measurement values comprises three or more discrete glucose measurement values.

6. The method of claim 5, wherein the further time interval occurs one time interval after the series of glucose measurement values.

7. The method of claim 5, wherein said predicting of the glucose measurement value at a further time interval is carried out using said series of three or more glucose measurement values in a series function represented by:

$$y_{n+1} = y_n + \alpha(y_n - y_{n-1}) + \frac{\alpha^2}{2}(y_n - 2y_{n-1} + y_{n-2}) \quad (7)$$

wherein y is the measurement value of glucose, n is the time interval between glucose measurement values, and α is a real number between 0 and 1.

8. The method of claim 7, wherein the series function is used to predict the value of $y_{n+1}$ wherein time interval occurs one time interval after the series of glucose measurement values is obtained.

9. The method of claim 1, wherein a sample comprising glucose is extracted from the subject into one or more collection reservoirs to obtain an amount or concentration of glucose in a reservoir.

10. The method of claim 9, wherein at least one collection reservoir comprises an enzyme that reacts with the extracted glucose to produce an electrochemically detectable signal to provide said raw signal.

11. The method of claim 9, wherein the one or more collection reservoirs are in contact with the skin or mucosal surface of the subject and the sample is extracted using an iontophoretic current applied to said skin or mucosal surface.

12. The method of claim 11, wherein said enzyme is glucose oxidase.

13. A glucose monitoring system for measuring glucose in a subject, said system comprising, in operative combination:
    a sensing mechanism in operative contact with the subject or with a glucose-containing sample extracted from the subject, wherein said sensing mechanism obtains a raw signal specifically related to glucose amount or concentration in the subject;
    a first device to obtain skin conductance readings or temperature reading from the subject; and
    one or more microprocessors in operative communication with the sensing mechanism, wherein said microprocessors comprise programming to (i) control the sensing mechanism to obtain a series of raw signals at selected time intervals, (ii) correlate the raw signals with glucose measurement values indicative of the amount or concentration of glucose present in the subject to obtain a series of glucose measurement values, (iii) predict a glucose measurement value at a further time interval, subsequent to obtaining the series of glucose measurement values, (iv) compare said predicted glucose measurement value to a threshold glucose value, wherein a predicted glucose measurement value less than or equal to the threshold glucose value is designated to be hypoglycemic, (v) control the first device to measure skin conductance readings or temperature readings of the subject, (vi) compare said skin conductance readings or temperature readings with a threshold skin conductance or temperature value or trend of skin conductance or temperature values to determine whether said skin conductance readings or temperature readings indicate a hypoglycemic event, and (vii) predict a hypoglycemic event in said subject when both (a) comparing said predicted glucose measurement value to said threshold glucose value indicates a hypoglycemic event at said further time interval, and (b) comparing said skin conductance readings or temperature readings with a threshold skin conductance or temperature value or trend of skin conductance or temperature values indicate a hypoglycemic event.

14. The monitoring system of claim 13, wherein the sensing mechanism comprises a biosensor having an electrochemical sensing element.

15. The monitoring system of claim 13, wherein the sensing mechanism comprises a near-IR spectrometer.

16. The monitoring system of claim 13, wherein said first device to obtain said skin conductance readings is a sweat probe.

17. The monitoring system of claim 13, wherein said first device to obtain said temperature readings is a temperature probe.

18. The monitoring system of claim 13, further comprising a second device and wherein said first device comprises a sweat probe to obtain said skin conductance readings and said second device comprises a temperature probe to obtain said temperature readings.

19. The monitoring system of claim 18, wherein both skin conductance readings and temperature readings are used to predict the likelihood of a hypoglycemic event.

20. The monitoring system of claim 13, wherein the selected time intervals are evenly spaced.

21. The monitoring system of claim 13, wherein the series of glucose measurement values obtained comprises three or more discrete glucose measurement values.

22. The monitoring system of claim 21, wherein the further time interval occurs one time interval after the series of glucose measurement values.

23. The monitoring system of claim 21, wherein said predicting of the glucose measurement value at a further time interval is carried out using said series of three or more glucose measurement values in a series function represented by:

$$y_{n+1} = y_n + \alpha(y_n - y_{n-1}) + \frac{\alpha^2}{2}(y_n - 2y_{n-1} + y_{n-2}) \quad (7)$$

wherein y is the measurement value of glucose, n is the time interval between glucose measurement values, and $\alpha$ is a real number between 0 and 1.

24. The monitoring system of claim 23, wherein the series function is used to predict the value of $y_{n+1}$ wherein time interval n+1 occurs one time interval after the series of glucose measurement values is obtained.

25. One or more microprocessors comprising programming to:

(i) control a sensing mechanism to obtain a series of raw signals at selected time intervals, wherein each raw signal is related to an amount or concentration of glucose in a subject;

(ii) correlate the raw signals with glucose measurement values indicative of the amount or concentration of glucose present in the subject to obtain a series of glucose measurement values;

(iii) predict a glucose measurement value at a further time interval, subsequent to obtaining the series of glucose measurement values;

(iv) compare said predicted glucose measurement value to a threshold glucose value, wherein a predicted glucose measurement value less than or equal to the threshold glucose value is designated to be hypoglycemic;

(v) control a first device to measure skin conductance readings or temperature readings of the subject;

(vi) compare said skin conductance readings or temperature readings with a threshold skin conductance or temperature value or trend of skin conductance or temperature values to determine whether said skin conductance readings or temperature readings indicate a hypoglycemic event; and (vii) predict a hypoglycemic event in said subject when both (a) comparing said predicted glucose measurement value to said threshold glucose value indicates a hypoglycemic event at said further time interval, and (b) comparing said skin conductance readings or temperature readings with a threshold skin conductance or temperature value or trend of skin conductance or temperature values indicates a hypoglycemic event.

26. The one or more microprocessors of claim 25, wherein the sensing mechanism comprises a biosensor having an electrochemical sensing element.

27. The one or more microprocessors of claim 25, wherein the sensing mechanism comprises a near-IR spectrometer.

28. The one or more microprocessors of claim 25, further comprising programming to control a second device, wherein said first device provides skin conductance readings and said second device provides temperature readings.

29. The one or more microprocessors of claim 28, wherein both skin conductance readings and temperature readings are used to predict the likelihood of a hypoglycemic event.

30. The one or more microprocessors of claim 25, wherein the selected time intervals are evenly spaced.

31. The one or more microprocessors of claim 25, wherein the further time interval occurs one time interval after the series of glucose measurement values.

32. The one or more microprocessors of claim 25, wherein the series of glucose measurement values obtained comprises three or more discrete glucose measurement values.

33. The one or more microprocessors of claim 32, wherein the predicting of the glucose measurement value at a further time interval is carried out using said series of three or more glucose measurement values in a series function represented by:

$$y_{n+1} = y_n + \alpha(y_n - y_{n-1}) + \frac{\alpha^2}{2}(y_n - 2y_{n-1} + y_{n-2}) \quad (7)$$

wherein y is the measurement value of glucose, it is the time interval between glucose measurement values, and $\alpha$ is a real number between 0 and 1.

34. The one or more microprocessors of claim 33, wherein the series function is used to predict the value of $y_{n+1}$ wherein time interval n+1 occurs one time interval after the series of glucose measurement values is obtained.

* * * * *